(12) United States Patent
Ravkin

(10) Patent No.: US 6,259,807 B1
(45) Date of Patent: Jul. 10, 2001

(54) IDENTIFICATION OF OBJECTS OF INTEREST USING MULTIPLE ILLUMINATION SCHEMES AND FINDING OVERLAP OF FEATURES IN CORRESPONDING MULTIPLE IMAGES

(75) Inventor: Ilya Ravkin, Palo Alto, CA (US)

(73) Assignee: Applied Imaging Corp., Santa Clara, CA (US)

(*) Notice: Subject to any disclaimer, the term of this patent is extended or adjusted under 35 U.S.C. 154(b) by 0 days.

(21) Appl. No.: 09/443,949

(22) Filed: Nov. 19, 1999

Related U.S. Application Data

(63) Continuation-in-part of application No. 09/072,502, filed on May 4, 1998.
(60) Provisional application No. 60/046,470, filed on May 14, 1997.

(51) Int. Cl.[7] .................................................. G06K 9/00
(52) U.S. Cl. ............................................................. 382/133
(58) Field of Search .................................... 382/129, 133, 382/134, 128; 435/5, 7.2, 6; 210/806; 356/39

(56) References Cited

U.S. PATENT DOCUMENTS

| | | |
|---|---|---|
| 3,999,047 * | 12/1976 | Green .................................... 382/134 |
| 4,125,828 * | 11/1978 | Resnick et al. ....................... 382/134 |
| 5,093,866 | 3/1992 | Douglas-Hamilton et al. .. 364/413.1 |
| 5,162,990 | 11/1992 | Odeyale et al. .................... 364/413.1 |
| 5,294,799 | 3/1994 | Aslund et al. ..................... 250/458.1 |
| 5,432,054 | 7/1995 | Saunders et al. ......................... 435/2 |
| 5,629,149 * | 5/1997 | Santamaria et al. ..................... 435/6 |
| 5,662,813 * | 9/1997 | Sammons et al. .................... 210/806 |
| 5,764,792 * | 6/1998 | Kennealy .............................. 382/133 |
| 5,989,835 * | 11/1999 | Dunlay et al. ......................... 435/7.2 |

FOREIGN PATENT DOCUMENTS

| | | | |
|---|---|---|---|
| 0732 582 A2 | 1/1996 | (EP) ............................... G01N/21/64 |
| WO 94/02830 | 2/1994 | (WO) ............................. G01N/1/30 |
| WO 97/05562 | 2/1997 | (WO) .............................. G06K/9/36 |
| WO 97/26617 | 7/1997 | (WO) .............................. G06K/9/00 |

OTHER PUBLICATIONS

Bianchi, Diana W. et al., "PCR quantitation of fetal cells in maternal blood in normal and aneuploid pregnancies," *Am.J.Hum.Genet.* 61:822–829 (1997).

Ravkin, Ilya et al., "Automated microscopy system for detection and genetic characterization of fetal nucleated red blood cells on slides," *SPIE*, Reprinted from: Proceedings of Optical Investigation of Cells In Vitro and In Vivo, vol. 3260, pp. 180–191 (Jan. 25–28, 1998, San Jose, CA).

Ravkin, Ilya et al., "Automatic counting of FISH spots in interphase cells for prenatal characterization of aneuploidies," *SPIE*, Reprinted from: Proceedings of Optical Diagnostics of Living Cells II, vol. 3604, pp. 208–217 (Jan. 25–26, 1999, San Jose, CA).

* cited by examiner

Primary Examiner—Andrew W. Johns
Assistant Examiner—Shervin Nakhjavan
(74) Attorney, Agent, or Firm—Townsend and Townsend and Crew LLP

(57) ABSTRACT

Detection of fetal nucleated red blood cells (NRBCs) is achieved by employing a combination of brightfield and fluorescence images of nuclear and cytoplasmic markers. The brightfield and fluorescence images are all obtained with a single multibandpass dichroic mirror. The objects in the sample are stained with a fluorescent dye that selectively stains nuclei and a dye that selectively stains fetal hemoglobin in the cytoplasm of fetal RBCs. UV excitation provides fluorescent emissions from the stained cell nuclei and visible illumination provides brightfield transmission of light that is absorbed by the stained cytoplasm. The images are processed to determine regions where the fluorescent emissions by cell nuclei in response to the UV excitation and the absorption by fetal hemoglobin of the brightfield illumination overlap or are in close proximity. The brightfield and fluorescence images may be sequentially acquired or derived from a single image where the UV excitation and visible illumination occur simultaneously.

17 Claims, 6 Drawing Sheets

IDENTIFICATION OF OBJECTS OF INTEREST USING MULTIPLE ILLUMINATION SCHEMES AND FINDING OVERLAP OF FEATURES IN CORRESPONDING MULTIPLE IMAGES

CROSS-REFERENCE TO RELATED APPLICATIONS

This application is a continuation-in-part of U.S. patent application Ser. No. 09/072,502, filed May 4, 1998, of Ilya Ravkin for "Identification of Objects of Interest using Multiple Illumination Schemes and Finding Overlap of Features in Corresponding Multiple Images," which claims priority from U.S. Provisional Application No. 60/046,470, filed May 14, 1997, of Ilya Ravkin for "Identification of Target Features Such As Nucleated Red Blood Cells Using Fluorescence and Transmission Scanning." The entire disclosures of both applications, including all attached documents and appendices, are incorporated by reference for all purposes.

BACKGROUND OF THE INVENTION

The present invention relates generally to image processing, and more particularly to identifying objects of interest in a sample.

It is known to perform image processing on images of biological samples where different dyes are caused to reside on different portions of the sample, each dye residing on a particular feature that characterizes an object of interest. The sample is then illuminated and imaged in a manner that the different features of interest can be distinguished from each other and from the background. This typically entails acquiring separate images using the appropriate light sources, filters, and optical setup so that each image's particular type of feature appears recognizably.

It is also known that certain brightfield dyes, while nominally assumed to stain different portions of the sample, are not perfectly selective, and stain both features of interest and features not of interest. For example, a dye that is considered to stain nuclei will often also, to a lesser extent, stain cytoplasmic structures. Further, many of the dyes in common use are characterized by a broad absorption spectrum, and therefore objects stained with the dye may show up in images acquired with a different illumination scheme.

SUMMARY OF THE INVENTION

The present invention provides robust and efficient techniques for analyzing samples to find objects of interest that are interspersed with other objects.

In short, a sample is prepared to impart optical properties to objects so that objects of interest, when imaged on an imaging medium under a plurality of different illumination schemes, exhibit a combination of features that is different from combinations of features exhibited by other objects. This combination is therefore referred to as the unique combination. The objects of interest arc found by analyzing images arising from the respective illumination schemes to determine instances where the unique combination of features from the different images meets a predetermined proximity constraint (e.g., overlap or near-overlap).

The illumination schemes and the optical properties are preferably such that the sample is imaged on the imaging medium under the plurality of different illumination schemes without having to move any optical elements into or out of the path between the sample and the imaging medium. Thus, images corresponding to the illumination schemes are largely immune to registration problems, thereby making the overlap of the unique combination of features a reliable indication of an object of interest.

The images can be separately acquired images, each taken with a respective one of the illumination schemes, or can be derived from a lesser number of images, each taken with a combination of the illumination schemes in effect simultaneously. Moreover, multiple images, corresponding to different illumination schemes, can be combined to form a pre-combined image. This pre-combined image can then be treated as one of the images whose features are input to the analysis to determine the proximity constraint.

In a specific example: the objects of interest are fetal nucleated red blood cells (NRBCs) and the other objects include non-nucleated red blood cells (RBCs) and nucleated white blood cells (WBCs); the objects in the sample are stained with a fluorescent dye that selectively stains nuclei and a dye that selectively stains fetal hemoglobin in the cytoplasm of fetal RBCs; there are two different illumination schemes, namely UV excitation to provide fluorescent emissions from the stained cell nuclei and brightfield transmission of light that is absorbed by the stained cytoplasm; and the unique combination of features is the fluorescent emissions by cell nuclei in response to the UV excitation and the absorption by fetal hemoglobin of the brightfield illumination.

In a specific example of a pre-combined image: the objects of interest are micrometastatic cells in bone marrow and the other objects include normal cells; the objects in the sample are stained with a dye that selectively stains nuclei and a dye that selectively stains cytoplasms of cells expressing cytokeratin; the illumination schemes include two brightfield transmissions using two different color filters; and the pre-combined image is a linear combination of the two images. In a more specific instance of this example: the dyes are hematoxylin, which stains nuclei, and new fuschin, which stains cytoplasms of cells positive for cytokeratin; the two illumination schemes are broadband illumination through a red filter and a green filter.

In specific embodiments, the image that is expected to contain the fewest features is analyzed first to determine candidate regions of interest for subsequent processing. This is accomplished by finding regions in the image that contain the feature that objects of interest (as well as other objects) exhibit in the image, and then examining the corresponding regions in the images to determine whether or not the images all contain instances of the respective features in sufficient proximity to denote the presence of an object of interest.

In specific embodiments, the images (or preferably candidate regions thereof) are processed to generate respective contrast masks, which are combined and further processed to provide the locations of objects of interest in the images. The combination can include a logical AND operation between the masks, possibly themselves morphologically dilated to form a seed image. The further processing can include reconstructing the seed within the masks to provide the desired regions representing the features of interest where they denote the presence of an object of interest.

A further understanding of the nature and advantages of the present invention may be realized by reference to the remaining portions of the specification and the drawings.

DESCRIPTION OF SPECIFIC EMBODIMENTS

1. IMAGING OVERVIEW

Figure 1:
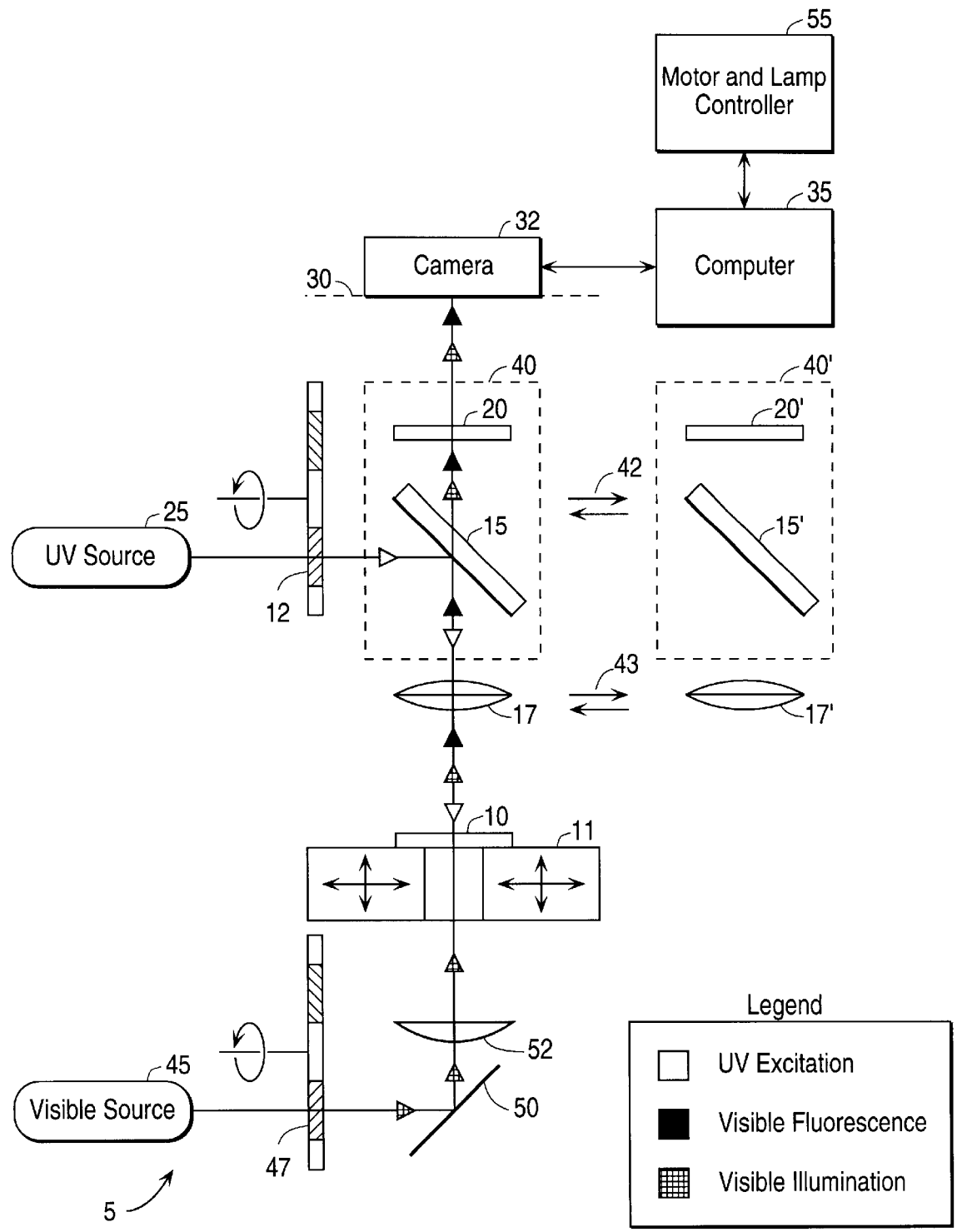
FIG. 1 is an optical schematic of apparatus according to an embodiment of the invention.

One embodiment utilizes fluorescence imaging in connection with brightfield (transmission) imaging to locate certain objects of interest in a sample. In the particular application, the samples are blood smears from pregnant women (9–16 weeks gestation) enriched for nucleated red blood cells (NRBCs), which are the objects of interest.

In the particular implementation, the identified objects are subjected to further analysis such as FISH. FISH stands for Fluorescence In-Situ Hybridization. A FISH sample is prepared by using a probe that binds to a particular DNA sequence in the chromosomes in the sample, and the probe is labeled with a fluorescent dye. M-FISH refers to using multiple probes, each of which binds to a different DNA sequence in the chromosomes in the sample, where each probe is labeled with a different dye or combination of two or more dyes. For that reason, the apparatus described below has additional functionality beyond what is needed for carrying out the invention.

A given fluorescent dye is characterized by an excitation (absorption) spectrum and an emission spectrum. The excitation and emission spectra are also sometimes referred to as the excitation and emission bands. Accordingly when the dye is irradiated with light at a wavelength within the excitation band, the dye fluoresces, emitting light at wavelengths in the emission band. Thus when the sample is irradiated with excitation radiation in a frequency band that excites a given dye, portions of the sample to which the probe labeled with the given dye is attached fluoresce. If the light emanating from the sample is filtered to reject light outside the given dye's emission band, and then imaged, the image nominally shows only those portions of the sample that bind the probe labeled with the given dye.

2. THE SAMPLE

2.1 Detection of of Fetal NRBCs

Although the details of the sample preparation are not part of the invention, the preparation will be described briefly to provide context for the description of the specific embodiments. The present invention may be used in the second phase of a three-phase evaluation that includes enrichment of fetal NRBCs from maternal blood, positive identification of fetal NRBCs, and genetic analysis of fetal NRBCs. As mentioned above, in specific implementations, the apparatus is configured so as to be suitable to play a role in both the second phase (identification) and third phases (genetic analysis).

The enrichment procedure starts with 20 mL of EDTA anticoagulated whole blood from pregnant women at 9 to 16 weeks post conception. It is calculated from PCR studies [Bianchi97] that this amount of blood contains approximately from 20 to 100 fetal cells. The goal is to achieve a 10,000-fold reduction of maternal blood cells without significant loss of the target NBRCs. This will permit the deposition of the fetal NRBC on a slide. The first step of enrichment is the separation of the blood sample into density fractions by centrifugation of the whole blood in a specially designed plastic tube [Saunders95]. The NRBCs are harvested from the interface layer between white blood cells (WBCs) and red blood cells (RBCs). The second step is a selective lysis of the remaining maternal RBCs. The third and final step separates NRBCs from the remaining WBCs in a three-layer density gradient formed of a silica colloid Percoll (Pharmacia, Uppsala, Sweden) suspended in gelatin under hypertonic conditions. After centrifugation, the NRBCs are harvested from the bottom of the gradient and deposited on a slide.

The resulting slide contains NRBCs, RBCs, and WBCs, all of them of possible fetal or maternal origin. In embodiments of the invention, a set of features that identify the fetal NRBCs are created to distinguish them from other types of cells. This is done by creating one type of contrast in cells containing fetal hemoglobin, and another type of contrast in cells having a nucleus. The slide is first reacted with the primary antibody, namely mouse anti fetal hemoglobin (HbF), then with the secondary antibody, namely goat anti mouse conjugated to biotin, and lastly streptavidin conjugated with alkaline phosphatase is added followed by Vector Blue substrate. The result is a blue precipitate on the cytoplasm of cells that contain fetal hemoglobin. A DNA intercalating agent (DAPI) gives all nuclei a fluorescent blue stain; the presence of both these contrasts determines a fetal NRBC.

2.2 Detection of Micrometastatic Cells Using Pre-Combined Image

Bone marrow preparation was stained with hematoxylin, which stains nuclei, and new fuschin, which stains cytoplasms of cells expressing cytokeratin. While these dyes are in widespread use, it is recognized that they are not ideal dyes, since they possess relatively broad absorption bands. It is also noted that the object of interest is visually distinguishable when illuminated with white light.

2.3 Custom Slides

Custom slides were developed for use with the invention. These slides have four painted squares in the corners with crosses laser etched in each square. Prior to scanning, coordinates of the reference points are recorded in the scan data file. At any time later, the reference points can be easily found and centered in the camera field of view. The offset is used for accurate relocation to all other objects in the scan file.

3. OPTICAL SYSTEM

FIG. 1 is a schematic showing a representative microscope system 5 for carrying out combined fluorescence (preferably epi-illuminated) and brightfield (transmission) imaging of a sample 10 according to the present invention. The sample is shown mounted to a stage 11, which provides three-dimensional rectilinear motion. As will be described below, the invention can be implemented with sequential acquisition of brightfield and fluorescent images, or with simultaneous acquisition of brightfield and fluorescent image components, with subsequent separation into separate images. The optical system includes portions for each of the two types of images, although a significant portion of the optics are shared.

The portion of the optical train for epi-illuminated fluorescence imaging includes an excitation filter 12 (shown as one of several such filters on a filter wheel), a polychroic mirror 15, a microscope objective 17 (say 10–100×), and an emission filter 20. The present invention can be implemented with a single excitation filter, a dichroic mirror, and an emission filter with a single passband. However, it is preferred to perform additional fluorescent measurements (FISH), and therefore it is preferred to use a multiband emission filter and a polychroic mirror so that multiple fluorescent images can be acquired without changing the mirror or emission filter.

Excitation radiation from an ultraviolet (UV) source 25 passes through excitation filter 12, is largely reflected by mirror 15 and proceeds through the microscope objective 17 to sample 10. The excitation light traveling toward the sample is shown schematically by hollow arrowheads. Fluorescent radiation emitted from sample 10 passes back through objective 17, through mirror 15, and through emission filter 20 to form an image in an image plane 30. The fluorescent light traveling away from the sample is shown schematically by solid black arrowheads. The image is digitized by a CCD video camera 32 and the digitized image is sent to a computer 35 for subsequent processing. Computer 35 is also used to control various components in the system, as will be described below.

Polychroic mirror 15 and emission filter 20 are typically rigidly mounted to a supporting structure 40 (shown in phantom); the assembly is often referred to as a cube, with multiple cubes being movable into and out of the optical path. Oppositely directed arrows 42 represent a suitable mechanism such as a rotatable turret or a detented slide mechanism. The multiple excitation filters are typically deployed on a rotatable filter wheel (as shown). In a typical microscope, objective lens 17 will be one of several mounted on a turret or like structure. This is shown schematically by oppositely directed arrows 43.

The portion of the optical train for the brightfield imaging includes a visible light source 45, a passband filter 47 (shown as one of several such filters on a filter wheel), a mirror 50, and a condenser 52. Illumination radiation from source 45 passes through passband filter 47, is reflected by a mirror 50 to condenser 52. The radiation passing through the condenser illuminates sample 10, and proceeds through microscope objective 17. The illumination radiation is in a wavelength range that passes through polychroic mirror 15 and emission filter 20. The visible illumination light is shown schematically by hatched arrowheads.

The system also includes a series of motor and lamp controllers, shown as a single controller block 55 interfaced to computer 35. Controller 55 controls various of the elements shown in the optical schematic of FIG. 1. This includes controlling motors for microscope focus, the filter wheels for excitation filter 12 and transmission filter 47, sample stage 11, cube turret 42, and objective turret 43. Controller 100 also controls UV light source 25 and visible light source 45. It should be understood, however, that the invention does not require that all the controllable elements be under computer control, although it is preferred to have the controls mentioned. The particular techniques for interfacing a computer to external instruments are known to those skilled in the art, and since they are not, per se, part of the invention, they will not be described further.

In specific implementations, the microscope is an Olympus BX-60 microscope (Olympus America, Inc., Melville, N.Y.), and includes transmission and fluorescence capabilities, a trinocular head, and 10×, 20×, and 40×objectives. Stage 11 can be a single or a multi-slide scanning stage (Maerzhauser Co., Upper Saddle River, N.J.), and is mounted on the microscope with a 7-position transmission filter wheel, a 12-position fluorescence filter wheel, and a focus drive (TOFRA, Palo Alto, Calif.). These devices are driven by stepping motors and are controlled by microstepping motor controllers (Intelligent Motion Systems, Marlborough, Conn.) Video camera 32 has light integration capability (COHU 4910, Cohu, Inc., San Diego, Calif.), and is coupled to a frame grabber board, which includes a 10-bit ADC and frame averaging. UV source 25 is typically a mercury arc lamp while visible light source 47 is typically a halogen lamp.

As will be described in greater detail below, in one example, the optical configuration of FIG. 1 is used for the sequential or simultaneous detection of DAPI fluorescence and Vector Blue absorption, and subsequently also for FISH imaging. That is, one image is generated possibly containing features characterized by DAPI fluorescence and another image is generated possibly containing features characterized by Vector Blue absorption.

In the specific implementation, the epi-illumination starts with the mercury arc, traverses the DAPI excitation filter and is reflected down by the polychroic mirror; excites the blue fluorescence of the DAPI stained cells, the emitted light returns through the objective, and passes through both the mirror and the emission filter to the camera. The transillumination starts with the halogen lamp, passes through a long-pass (red) filter, is absorbed by the cells stained with Vector Blue, and passes through the objective, the polychroic mirror and emission filter to the camera. Depending on the DNA probes, a Chroma 83000 triple band filter set (Chroma Technology Corp., Brattleboro, Vt.) or a Vysis quad DAPI/Aqua/Green/Orange filter set (Vysis, Inc., Downers Grove, Ill.) is used. Transmission Kohler illumination and the spectral filter optimize contrast for the cytoplasmic color on the slide. These two images may be obtained from separate epi-illumination and transillumination of the sample, or may be extracted from a single image that is acquired during a period of simultaneous epi-illumination and trans-illumination of the sample.

In another example, where the sample was stained with hematoxylin and new fuschin the optical configuration of FIG. 1 is used for the generation of one image possibly containing features characterized by the absorption of broadband light that has passed through a green filter and the subsequent generation of another image possibly containing features characterized by absorption of broadband light that has passed through a red filter. As will be described in more detail below the two images are combined in a linear fashion to provide what is referred to as a pre-combined image.

Depending on the application, the pre-combined image may be used in conjunction with another image obtained with a third illumination scheme.

4. COMPUTER SYSTEM

Figure 2:
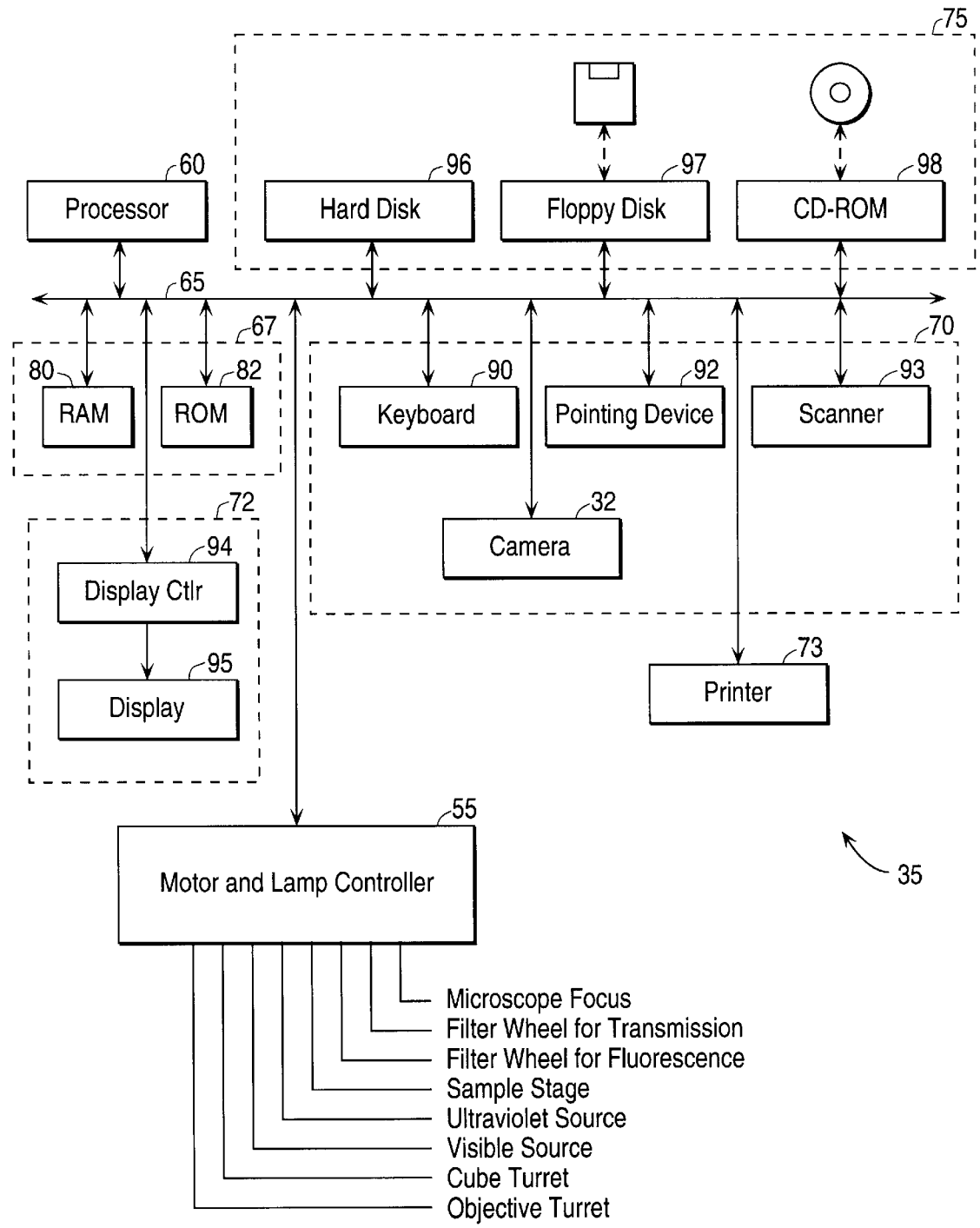
FIG. 2 is a block diagram of a computer system according to an embodiment of the invention.

FIG. 2 is a simplified block diagram of computer 35. The computer is used to control all motion, perform image acquisition and processing, and user interface functions. In a specific implementation, computer 35 is a workstation running the Windows 95 operating system (MicroSoft Corporation, Redmond, Wash.). In accordance with known practice, the computer system includes a processor 60 that communicates with a number of peripheral devices via a bus subsystem 65. These peripheral devices typically include a memory subsystem 67, an input facility 70, a display subsystem 72, output devices such as a printer 73, and a file storage system 75.

In this context, the term "bus subsystem" is used generically so as to include any mechanism for letting the various components of the system communicate with each other as intended. With the exception of some of the input devices and the display, the other components need not be at the same physical location. Thus, for example, portions of the file storage system could be connected via various local-area or wide-area network media, including telephone lines. Similarly, the input devices and display need not be at the same location as the processor, although it is anticipated that the present invention will most often be implemented in the context of PCs and workstations.

Bus subsystem 65 is shown schematically as a single bus, but a typical system has a number of buses such as a local bus and one or more expansion buses (e.g., ADB, SCSI, ISA, EISA, MCA, NuBus, or PCI), as well as serial and parallel ports. Network connections are usually established through a device such as a network adapter on one of these expansion buses or a modem on a serial port. The computer system may be a desktop system or a portable system.

Memory subsystem 67 includes a number of memories including a main random access memory (RAM) 80 and a read only memory (ROM) 82 in which fixed instructions are stored. In the case of Macintosh-compatible personal computers the ROM would include portions of the operating system; in the case of IBM-compatible personal computers, the ROM would include the BIOS (basic input/output system).

Input facility 70 typically includes a user input device such as a keyboard 90, and may further include a pointing device 92 and a scanner 93. The pointing device may be an indirect pointing device such as a mouse, trackball, touchpad, or graphics tablet, or a direct pointing device such as a touchscreen incorporated into the display. Other types of user input devices, such as voice recognition systems, are also possible. Camera 32 can be considered part of the input facility.

Display subsystem 72 typically includes a display controller 94 and a display device 95 coupled to the display controller. The display device may be a cathode ray tube (CRT), a flat-panel device such as a liquid crystal display (LCD), or a projection device. Display controller provides control signals to the display device and normally includes a display memory (not shown in the figure) for storing the pixels that appear on the display device. The display subsystem may also provide non-visual display such as audio output.

The file storage system provides persistent (non-volatile) storage for program and data files, and typically includes at least one hard disk drive 96 and at least one floppy disk drive 97 (with associated removable media). There may also be other devices such as a CD-ROM drive 98 and optical drives (all with their associate removable media). Additionally, the system may include drives of the type with removable media cartridges. The removable media cartridges may, for example be hard disk cartridges, such as those marketed by Syquest, Iomega, and others, and flexible disk cartridges, such as those marketed by Iomega and others. As noted above, one or more of the drives may be located at a remote location, such as in a server on a local area network or at a site on the Internet's World Wide Web.

5. PROCESSING OVERVIEW

Figure 3:
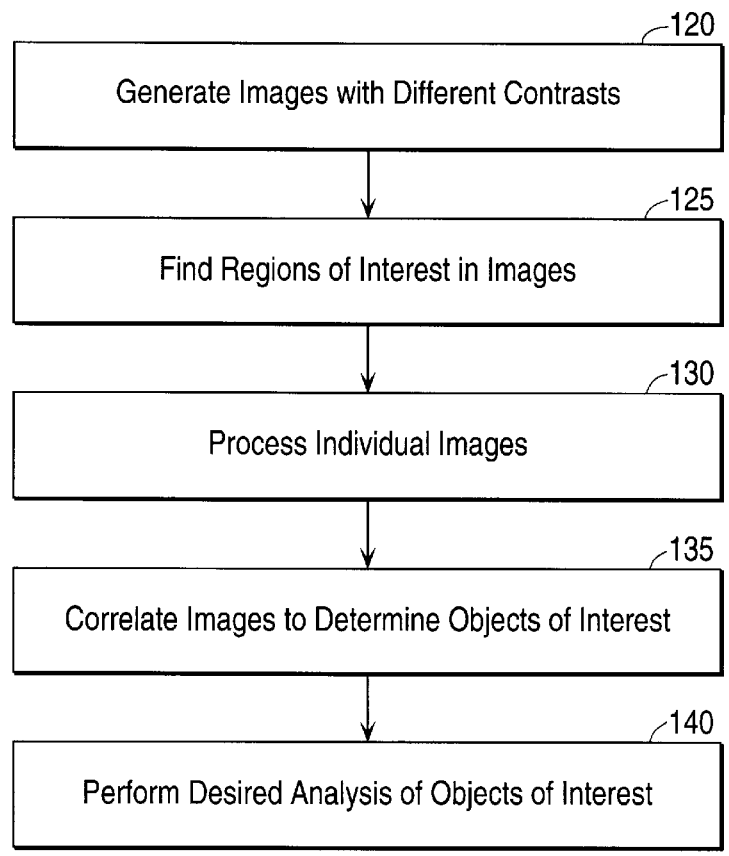
FIG. 3 is a flowchart showing the sequence of operations performed in specific embodiments of the invention.

FIG. 3 is a flowchart showing, at a high level, the sequence of operations performed in specific embodiments of the invention. As mentioned above, the invention is directed toward finding specific objects of interest in an sample. In one specific application, the objects of interest are fetal nucleated red blood cells (NRBCs) in a sample of maternal blood. Despite enrichment, the number of NRBCs is likely to be small compared to the number of non-nucleated red blood cells (RBCs) and nucleated white blood cells (WBCs).

The analysis begins at a step 120 of generating images with two different contrasts, one which shows regions of cytoplasm and one which shows nuclei. As mentioned above, these two contrasts arise from the absorption of transmitted visible (red) light by the (blue) dye that preferentially stains cytoplasm and the fluorescence from cell nuclei stained by the fluorescent dye DAPI. Further, as mentioned above, the two images can be generated from separately acquired images resulting from sequential exposure of the sample to the two light sources, or can be generated from a single acquired image with the sample illuminated by both light sources simultaneously.

The images are generated for each of a plurality of fields on the slide. A field corresponds to the number of pixels on the CCD imaging array, typically 512×512, and there are typically hundreds or thousands of fields on the slide. This is accomplished by stepping sample stage 11 along both axes in the plane of the sample. Since the objects of interest are likely to occupy a relatively small fraction of the image field, it is preferred to perform a step 125 of quickly determining the portions of each field that are candidates for containing objects of interest. The subsequent processing steps in the method are recited as applying to the images, but it should be understood that the processing steps are typically only applied to the candidate regions of each field.

The individual images are processed separately at a step 130 to provide derivative images (masks) that can be correlated or combined at a step 135 to determine if an object of interest is present. The method has thus provided the locations of regions of the sample that are expected to contain objects of interest, making it possible to subject the objects to further analysis at a step 140. For example, in a subsequent analysis phase, the computer can control the stage to step the sample to these locations for manual inspection or further computerized processing. Thus, the result of the method is acceptance of an image as falling into a specific class of object, which is to be counted or to be examined in more detail for other contrasts, for example other colors of fluorescence for FISH analysis.

6. IMAGE ACQUISITION

6.1 Sequential Image Acquisition

With sequential illumination of the sample, separate brightfield and fluorescence images are acquired on every field. For the absorption image, epi-illumination is blocked by an opaque segment of the excitation filter wheel, and visible light source 45 sends red light through the specimen to the camera. The absorption image shows objects positive for antibody staining. For the fluorescence image, trans-illumination is blocked, and the specimen is excited by light from UV source 25 going down through the objective. The fluorescence image shows all nuclei in the field. Fetal NRBCs are the objects having dark cytoplasms in the absorption image and bright nuclei in the fluorescence image.

6.2 Simultaneous Image Acquisition

Figure 4A:
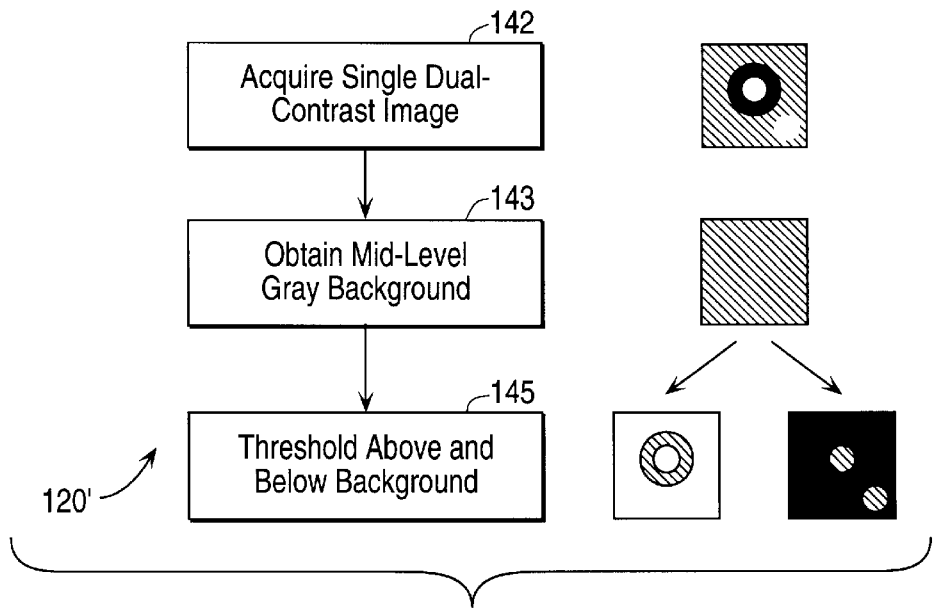
FIG. 4A is a flowchart showing image generation steps using simultaneous illumination of the sample.

FIG. 4A is a flowchart showing steps that can be performed to implement step 120 of FIG. 3 using simultaneous illumination of the sample. The reference number 120' is used to denote this variant. Also shown is a highly stylized view of a small portion of the images at each step. These stylized views show three levels, black, white, and gray (as represented by cross-hatching). The objects are shown as having a circular shape.

Figure 4B:
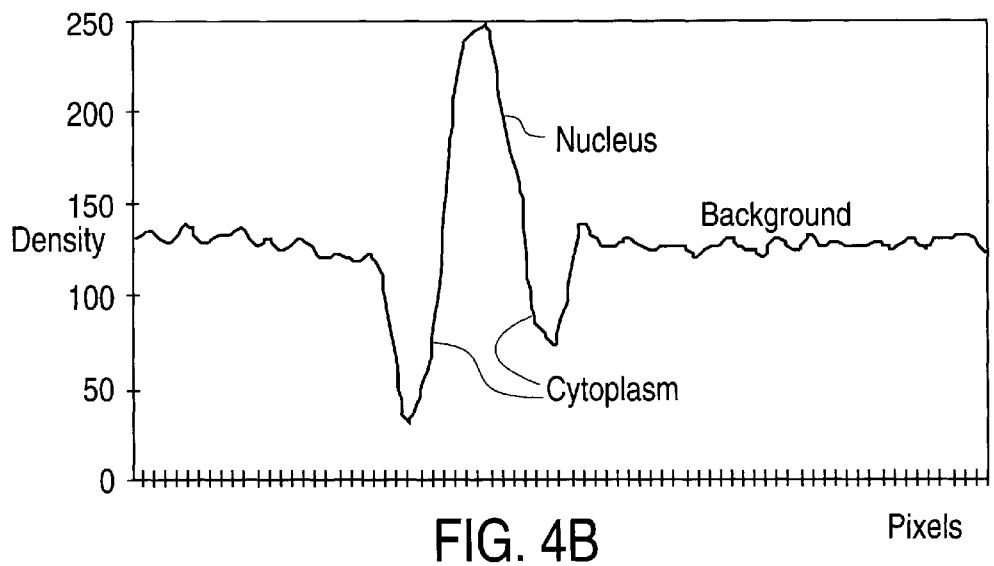
FIG. 4B is a combined light intensity profile through a fetal nucleated red blood cell (NRBC)

At a step 142, a single image is acquired with the sample being trans-illuminated with red light and epi-illuminated with UV light at the same time. The intensities of both illumination systems light are balanced so that the empty background corresponds to a mid-level gray. Antibody-stained objects (cytoplasm) appear darker than the background and DAPI-stained objects (nuclei) appear brighter than the background. FIG. 4B is a combined light intensity profile through a fetal NRBC, and shows a significant drop in the cytoplasm, a rise in the nucleus, and another drop in the cytoplasm. In the schematic representation, the image shows an NRBC having cytoplasm (black in the figure) surrounding nucleus (white in the figure), and another nucleus without surrounding cytoplasm (white in the figure), all against a gray background (hatched in the figure).

Since the two images have been combined optically, they need to be separated digitally. As a first step to this end, a background gray level is determined at a step 143. In a specific implementation, the mode is used. Thus, the whole field is measured and a histogram of the number of pixels at each possible intensity level is constructed. The histogram is smoothed by adjacent averaging and the intensity corresponding to the top of the highest peak in the histogram is defined as the background value of light intensity. It would also be possible to use an average pixel value to specify the mid-level gray.

The combined images are separated at a step 145 into a below-the-background component, characterizing antibody absorption, and an above-the-background component, characterizing DAPI fluorescence. This is accomplished by comparing the background value determined in step 143 to the image on a pixel-by-pixel basis. This process is similar to a subtraction with saturation. This produces separate positive and negative-going images, which are essentially the two separate contrasts dissected from the single image.

This process can be viewed, with reference to FIG. 4B, as follows. For the absorption image, add a value corresponding to the difference between the maximum intensity value (255) and the background intensity value to all pixels. This has the effect of bringing the cytoplasm trough regions up from near-black to mid-gray, bringing the background up to a white or near-white level, and clipping the fluorescence peak at white. For the fluorescence image, subtract the background intensity value from all pixels, thereby bringing the fluorescence peak down to mid-gray, bringing the background down to a black or near-black level, and clipping the cytoplasm regions to black.

6.3 Relative Merits of Sequential vs. Simultaneous Acquisition

Simultaneous illumination and image acquisition has the advantages of speed (because there is only one image to acquire and no filter switch for every field), and easy human recognition of NRBCs under the microscope. On the other hand, the disadvantage is a tighter requirement for cell fixation and sharpness of the DAPI image. There are conditions when the nuclear counterstain image is fuzzy and overlaps with the cytoplasm. In this case, simultaneous illumination cancels out both contrasts and the sequential method should be used. It should be realized, however, that the optical configuration is still advantageous for the sequential image acquisition since none of the elements in the optical path from the sample to the camera have to be moved, thus enhancing the ease of registration of the separate images for further processing. Naturally, where the two images were generated from a single combined image, they are automatically registered.

6.4 Pre-Combined Image

Figure 4C:
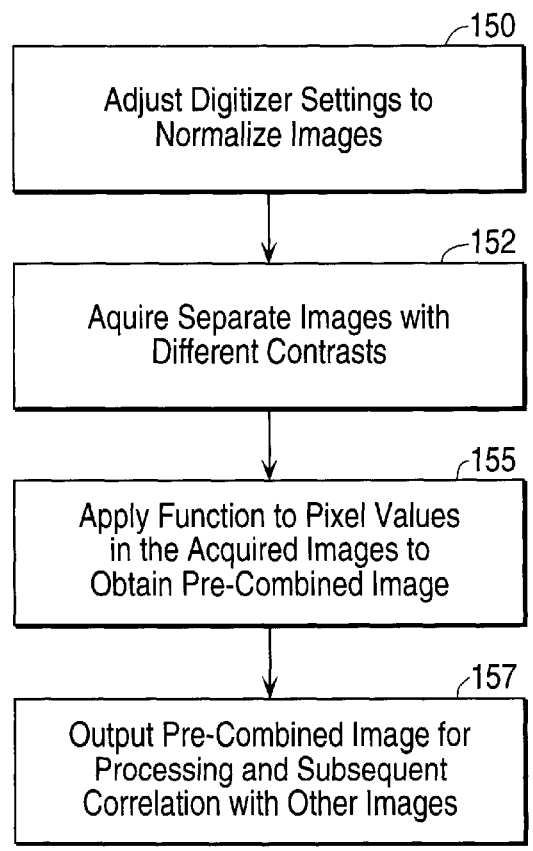
FIG. 4C is a flowchart showing generation of a pre-combined image from multiple images.

FIG. 4C is a flowchart showing steps for generating a pre-combined image from multiple images taken with different illumination schemes and/or different contrasts. A pre-combined image may be any functional, logical or mathematical combination of images representing different illumination schemes. That is, a pre-combined image is an image that depends on two or more images that represent different illumination schemes and/or different contrasts in the same illumination scheme. In the specific example, the pre-combined image is a linear combination of the absorption images acquired with a green filter (a given pixel value being referred to as G) and the absorption image acquired with a red filter (a given pixel value being referred to as R). The linear combination is given by:

$$F = k1*G + k2*R + k3$$

where in the particular example, k1=2, k2=−2, and k3≈255 (white). It is noted that a linear combination of images is often referred to as a color-corrected image. That is, a color-corrected image is a specific example of a pre-combined image.

This series of steps may be performed in connection with step 120 in FIG. 3, and is therefore designated 120". As mentioned above the two different contrasts are trans-illumination through a green filter and a red filter. It is generally preferred to perform a normalization step 150. For the particular example, the normalization entails adjusting the digitizer settings so that, for the majority of pixels, the darkness in both images is the same. In a particular embodiment, the controllable parameters are the low and high references for the digitizer (for each of the two image acquisitions). Due to color drifts and changes in pH, it has been found desirable to do periodic adjustments. For example, it has been found effective to determine a set of digitizer settings for the green image for each batch of slides, and to adjust the digitizer settings for the red image every 8–10 fields.

One technique for accomplishing this is to generate a histogram of the quantity k1*G+k2*R+128 and adjust the digitizer settings to make the histogram as symmetrical as possible. The use of the offset 128 is to maintain the values within the range of 0–255 since the digitized values are stored as 8-bit numbers. An alternative approach to adjusting the digitizer settings is to adjust the formula for the pre-combination after digitization has occurred. This possibility is not shown in the figure.

With the digitizer settings thus adjusted, the images are then acquired at a step 152, and combined at a step 155. The pre-combined image is then output at a step 157, and subjected to processing and correlation with other images, as shown in steps 125, 130, 135, and 140 in FIG. 3.

7. IMAGE PROCESSING AND CORRELEATION

7.1 Find Regions Potentially Containing Objects of Interest

As mentioned above, it is preferred to limit further refined processing to those regions of the image (or image field) that are considered likely to contain objects of interest. The NRBCs in the sample have a nucleus surrounded by cytoplasm containing fetal hemoglobin. In the images, this translates to an overlap or close proximity of an absorption feature and a fluorescence feature. In order to find corresponding regions in the respective images containing both features, it is necessary to scan one of the images for that image's distinctive feature. Once the scan of one image yields a set of candidate regions, it is only necessary to scan corresponding regions in the other image to determine whether they contain the other image's distinctive feature. This will be more efficient if the image that is expected to contain fewer features is scanned first. For example, if there are significantly more absorption features in the absorption image than fluorescent features in the fluorescence image, the fluorescence image should be scanned for features first. This order can be determined by the user, or set automatically as a function of the type of scan to be performed. The relative frequency of object types typically depends on the sample preparation (e.g., degree of enrichment).

Figure 5:
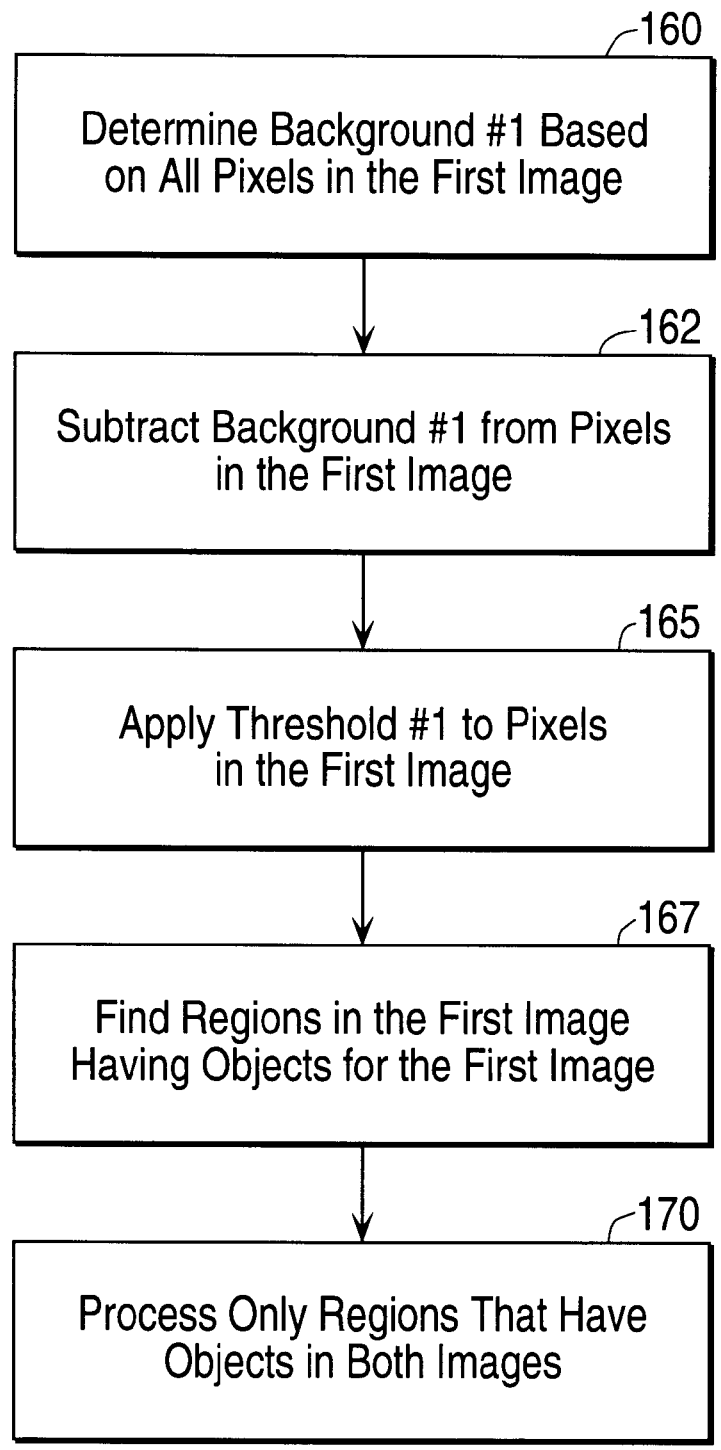
FIG. 5 is a flowchart showing steps for determining regions of interest.

FIG. 5 is a flowchart showing steps that can be performed to implement step 125 of FIG. 3. At this point in the overall process, separate absorption and fluorescence images have been provided, either having been acquired from separate optical images or having been electronically separated from a single optical image as shown in FIGS. 4A and 4B. The image that is expected to have fewer of its characteristic features will be referred to as the "first" image.

At a step 160, a background is determined for the first image based on all pixels in the first image. If the first image is the fluorescent image, the background value is set equal to the value of the darkest (lowest intensity value) pixel in the image. At a step 162, this background is subtracted from all the pixels in the image. At a step 165, all pixels are compared to a threshold for the image, to generate a binary image. A pixel is considered to be "ON" if it is above the threshold (fluorescent image) or below the threshold (absorption image). The threshold is relatively high, since at this stage it is only desired to see whether features are present without attempting to determine their precise outlines.

At a step 167, the image is analyzed to determine the locations of sufficiently large connected components (i.e., instances of a sufficient number of connected ON pixels) to signify the likely presence of an object. This is done using blob analysis according to techniques known to those skilled in the art. The regions surrounding the connected components in the first image define a set of candidate regions. These regions are significantly smaller than the 512×512 field, typically the smallest convenient square of pixels that can be defined, say 32×32 pixels or 64×64 pixels. At a step 170, coordinates for the set of candidate regions are stored for further analysis. As mentioned above, further processing is preferably restricted to these regions.

7.2 Mask Creation

Figure 6:
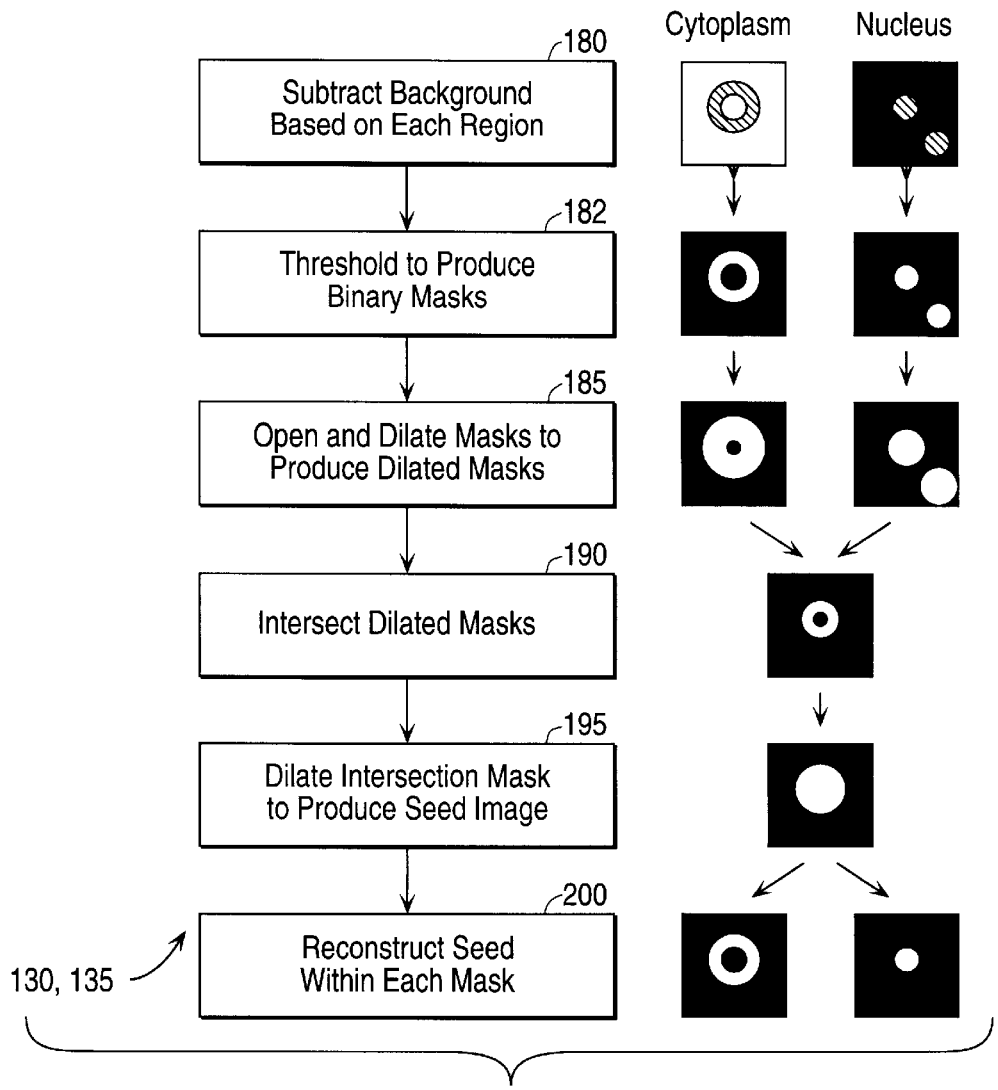
FIG. 6 is a flowchart showing steps for constructing two separate masks that represent nuclear contrast and cytoplasmic contrast.

FIG. 6 is a flowchart showing steps that can be performed to implement steps 130 and 135 of FIG. 3, namely separately processing the two images for a set of features which leads to the construction of two separate masks that represent nuclear contrast and cytoplasmic contrast. Input at this stage are the cytoplasm and nuclear images generated in step 120, with backgrounds having been subtracted at steps 162 and 172. As noted above, the further processing is done only on the image regions identified in step 125.

At a step 180, the images are subjected to further background subtraction operations, but this time the background is determined on a region-by-region basis. At a step 182, the images are thresholded to create binary masks. For the cytoplasm image, pixels darker than the threshold are set to ON (white in the figure) and pixels lighter than the threshold are set to OFF (black in the figure). For the nuclear image, pixels lighter than the threshold are set to ON (white) and pixels darker than the threshold are set to OFF (black).

When viewing the grayscale image(s), the notion of whether the features in the image(s) overlap tends to be rather subjective. Once the images have been thresholded to generate binary images, the separation is directly quantifiable. Depending on the threshold used to create the binary images and the objects' geometries, features that appear subjectively to an observer to overlap in the grayscale images may be disjoint, although in close proximity, in the binary images. It is then possible to define a maximum separation of the features (in the binary images) that will be still be considered to represent an overlap, and thus a candidate for the object of interest.

The specific feature of the cells of interest is the overlap or close proximity of antibody-positive and DAPI-positive areas. In order to find these overlaps or proximities, the binary masks are subjected at a step 185 to a first set of morphological image processing steps [Serra89]. In particular, the images are morphologically "opened" to eliminate small random signals which are not part of the identified localized feature. Opening is in effect a filtering process. The opened masks are then morphologically "dilated," which has the effect of expanding each remaining feature (region of ON pixels, shown as white in the figure) by a designated amount in all directions. Note that the dilation has the effect of shrinking holes (regions of OFF pixels surrounded by or intruding into regions of ON pixels.

The designated amount of expansion is determined by the morphological dilation operation. More specifically, the degree to which an edge of a region of ON pixels is expanded by dilation is determined by the size of what is referred to as a structuring element. Thus the size of the structuring element is selected in view of the amount by which features are allowed to be separated and still be considered to "overlap." This is a function of image magnification. It has been found that a structuring element that moves the boundaries by one pixel operates well at magnifications of 10×–20×. This means that two objects that just touch will, when dilated, have an overlap of two pixels.

An appropriate size for the structuring element can be empirically determined in a straightforward manner. For example, a representative sample of objects where the features appear to overlap in the grayscale images can be subjected to the thresholding, and the distribution of separations in the binary images determined. It has further been found that the results are not very sensitive to the size of the structuring element. For example, an expansion by two pixels would also likely be suitable.

At a step 190, the opened, dilated masks are combined or overlapped on the same field to discover true overlapping features. This is a logical AND operation that leaves only the rim of where the two masks overlap. This is also referred to as the intersection of the two masks. At a step 195, the intersection mask is morphologically dilated to produce a seed image. At a step 200, the seed image is used to finally identify the true cytoplasm and nuclear regions in the two images. This is done by reconstructing the seed within the cytoplasm and nuclear contrast images that were input to step 185. As can be seen in the figure, only the nucleus that had the surrounding cytoplasm appears in the final mask.

8. WORKFLOW AND PERFORMANCE

The workflow for analysis of slides consists of three major steps: scan, review, and probe acquisition (FISH). The first step starts with a slide and produces a data file, which contains images and measurements of detected objects. In the second step, the operator reviews results of the scan, classifies and annotates the cells, and selects cells of interest for probe acquisition. The review is done primarily from the screen images, but the slide is available for immediate relocation and inspection under the microscope. Finally, probe images of the selected cells are acquired and the probe spots are counted.

Figure 7:
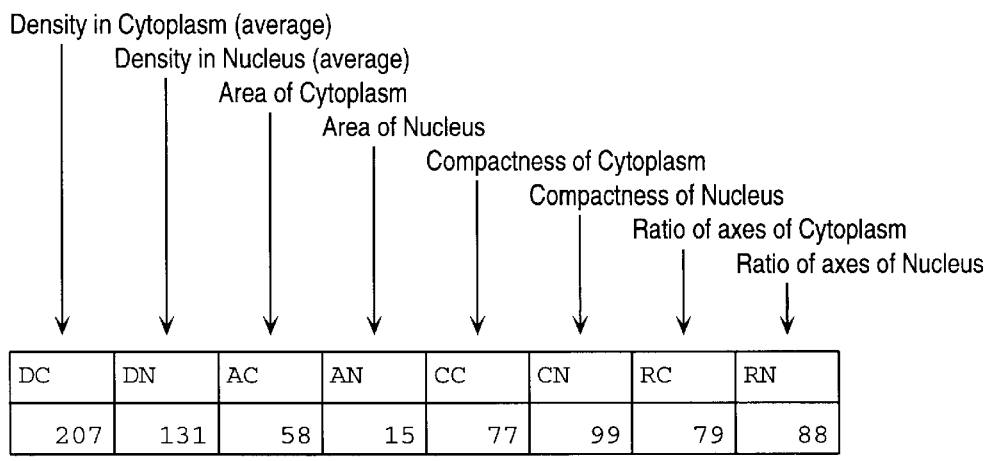
FIG. 7 shows a representative set of data that is generated and stored for each NRBC.

The main form of presenting information for review is in a data grid, which contains images, measured features, classification, and annotation. FIG. 7 shows a representative set of data that is generated and stored for each NRBC. Ratio of Axes is the ratio of the short main inertia axis to the long main inertia axis, normalized to the range [0–100]. Small values are typical for elongated shapes; large values are typical for objects that appear more nearly circular in the image. Compactness is the ratio of the moment of inertia of a disk with the same area as the given shape to the moment of inertia of the shape. This ratio is normalized to the range [0–100]. Small values are typical for ring-like, star-like or irregular shapes, large values are typical for compact and round objects.

To set up a scan the user performs the following actions:

Defines the scan area to correspond to the actual smear location on the slide.

Selects a representative field, and adjusts the image digitization parameters for each of the filters used in scanning. (Sometimes the digitizer adjustment is done on calibration slides).

Runs the finding algorithm on the selected field and adjusts the parameters if needed.

Sets the position of the reference point to provide for accurate relocation in the future.

Gives a name to the scan, and starts the scan.

The scan can be interrupted at any time to look at the objects and readjust parameters before resuming the scan. After the scan is complete, the user returns for review.

The objects can be revisited any number of times and each time a group of several images can be acquired for each object (for example, original images from scanning, same filter images at higher magnification, and probe images). Each group of images may be shown differently (e.g., in monochrome, in color, or both). The review process is aided by two-dimensional distribution plots of any two of the measured features. Each class in the distribution is shown in a different color and the display resembles that in flow cytometry. Switching of views among stored cell images, distribution of cells in the feature space, and microscope relocation is instantaneous.

Another useful facility is sorting by linear combination of the measured features, which presents cells for review in the order of most likely candidates first. The result of the review is a classification and selection of cells for probe acquisition. At this time, the finding algorithms are designed to look for objects of one class (defined by the algorithm and its parameters), and there is no further automatic classification in the feature space. Classification is done manually by the user.

Searching for one combination of features, namely the overlap of DAPI fluorescence and HbF antibody absorption, has proved to be robust, missing few cells (<3%). The false positives are the overlaps of RBCs, WBCs, and debris. To separate NRBCs from false positives, the following parameters are used: average and integrated intensity in nucleus and cytoplasm, and area and shape of the nucleus and of the union of nucleus and cytoplasm.

The speed for scanning a $4cm^2$ (typical smear) is ½ hour (at magnification 10×). The average relocation error is 2 mm (4 mm maximum). The program finds 97.2% of the NRBCs found by a trained operator.

9. REFERENCES

The following documents were referred to above and are hereby incorporated by reference in their entirety for all purposes:

[Bianchi97] D. W. Bianchi, J. M. Williams, L. M. Sullivan, F. W. Hanson, K. W. Klinger, A. P. Shuber, "PCR quantitation of fetal cells in maternal blood in normal and aneuploid pregnancies," Am. J. Hum. Genet. 61, pp. 822–829, 1997;

[Saunders95] A. M. Saunders, M. A. Zarowitz, P. J. Baldwin, "Method for separating rare cells from a population of cells," U.S. Pat. No. 5,432,054, issued Jul. 11, 1995; and

[Serra89] J. Serra, Image Analysis and Mathematical Morphology, Vol. 1. Academic Press, London, 1989.

10. CONCLUSION

In conclusion, it can be seen that the present invention provides methods and apparatus for efficiently and reliably identifying objects of interest in an image. A system according to the invention provides, in particular implementations, automated finding of cells, storage of cell images and their slide coordinates, with interactive review, classification, and selection by the operator. The invention is robust in the face of the high variation among specimens, and adapts to difference in staining intensity and probe brightness, type of cell deposition on slides (smear or cytospin), cell density, different kinds of samples, and prevalence of different cell types.

While the above is a complete description of specific embodiments of the invention, various modifications, alternative constructions, and equivalents may be used. For example, while it is preferred to have epi-illumination for the UV excitation, it is possible to use trans-illumination for the UV excitation. Similarly, while the specific embodiment is based around a standard microscope, it is possible to carry out the invention with a specially configured optical setup. Moreover, while the function that is used to generate the pre-combined image in the specific example is the linear combination, the ratio of the two images (computed on a pixel-by-pixel basis) could be used instead.

Therefore, the above description should not be taken as limiting the scope of the invention as defined by the claims.

What is claimed is:

1. A method of finding objects of interest that are interspersed with other objects in a sample, the method comprising:

providing a sample where objects have optical properties so that objects of interest, when imaged on an imaging medium under different illumination schemes, exhibit a combination of features, referred to as the unique combination, that is different from combinations of features exhibited by other objects;

generating multiple images by subjecting the sample to multiple illumination schemes;

applying a function to the multiple images to obtain a pre-combined image;

subjecting the sample to additional illumination schemes;

generating corresponding additional images wherein the additional images are derived from a lesser number of images, with at least one of the lesser number of images being taken with a combination of illumination schemes in effect simultaneously; and analyzing the pre-combined image and the additional images to determine instances where the unique combination of features from the different images meets a predetermined proximity constraint.

2. The method of claim 1 wherein the function is a linear combination.

3. The method of claim 1 wherein the function is a ratio.

4. The method of claim 1 wherein the illumination schemes include UV and visible illumination.

5. The method of claim 1 wherein all the additional images are acquired simultaneously.

6. The method of claim 1 wherein first and second of the additional images are derived from a single image by:

configuring the illumination schemes corresponding to the first and second of the additional images so that features corresponding to the first and second illumination scheme are respectively at intensities above and below a background level; and generating the first additional image by reducing each pixel value in the single image by a first amount so that background regions are generally at minimum intensity; and generating the second additional image by increasing each pixel value in the single image by a second amount so that background regions are generally at maximum intensity.

7. The method of claim 1 wherein analyzing the pre-combined image and the additional images comprises:

examining a particular image of the pre-combined image and the additional images to find a set of regions of the particular image that contains features; and analyzing only the corresponding regions of the pre-combined image and the additional images.

8. The method of claim 1 wherein analyzing the pre-combined image and the additional images comprises:

applying a threshold to each image to create a respective binary mask having ON pixels in areas representing the presence of features in that image;

morphologically processing each mask to expand regions of connected ON pixels; and logically ANDing the masks to define regions of overlap or near overlap of features present in the images.

9. The method of claim 1 wherein:

the objects of interest are fetal nucleated red blood cells (NRBCs) and the other objects include non-nucleated red blood cells (RBCs) and nucleated white blood cells (WBCs);

the objects in the sample are stained with a fluorescent dye that selectively stains nuclei and a dye that selectively stains fetal hemoglobin in the cytoplasm of fetal RBCs;

the plurality of different illumination schemes include UV excitation to provide fluorescent emissions from the stained cell nuclei and brightfield transmission of light that is absorbed by the stained cytoplasm; and the unique combination of features is the fluorescent emissions by cell nuclei in response to the UV excitation and the absorption by fetal hemoglobin of the brightfield illumination.

10. The method of claim 9 wherein the sample is illuminated by the UV excitation and brightfield transmission so as to generate a single image, and processing the single image comprises:

determining a background level for the single image;

generating a nuclear image by reducing pixel values in the single image by a first amount so that background regions are generally at minimum intensity;

generating a cytoplasm image by increasing pixel values in the single image by a second amount so that background regions are generally at maximum intensity;

processing the cytoplasm image to produce a cytoplasm contrast mask having regions representing the presence of cytoplasm;

processing the nuclear image to produce a nuclear contrast mask having regions representing the presence of cell nuclei; and combining the cytoplasm contrast mask and the nuclear contrast mask to determine regions of connected ON pixels in the cytoplasm contrast mask that arc sufficiently close to regions of connected ON pixels in the nuclear contrast mask to signify the likely presence of fetal nucleated red blood cells.

11. The method of claim 10 wherein processing the nuclear and cytoplasm images comprises:

examining one of the nuclear and cytoplasm images to find a set of regions of the one of the nuclear and cytoplasm images that contains features; and processing only the corresponding regions of the other of the nuclear and cytoplasm images.

12. The method of claim 10 wherein the cytoplasm contrast mask the nuclear contrast mask are combined by:

morphologically processing each mask to expand regions of connected ON pixels; and logically ANDing the masks, as morphologically processed, to define regions of overlap or near overlap of features present in the images.

13. A method of finding objects of interest that are interspersed with other objects in a sample, the method comprising:

providing a sample where objects have optical properties so that objects of interest, when imaged on an imaging medium under a plurality of different illumination schemes, exhibit a combination of features, referred to as the unique combination, that is different from combinations of features exhibited by other objects;

subjecting the sample to the plurality of illumination schemes;

generating a corresponding plurality of images;

for one or more subsets, each subset containing multiple ones of the plurality of images, applying a function to the multiple images in the subset to obtain one or more pre-combined images, each pre-combined image corresponding to a respective one of the subsets; and analyzing the one or more pre-combined images and one or more of the plurality of images to determine instances where the unique combination of features from the one or more of the pre-combined images and the one or more of the plurality of images meets a predetermined proximity constraint.

14. The method of claim 13 wherein the plurality of images are derived from a lesser number of images, with at least one of the lesser number of images being taken with a combination of illumination schemes in effect simultaneously.

15. The method of claim 13 wherein the function is a linear combination.

16. The method of claim 13 wherein the function is a ratio.

17. The method of claim 13 wherein one of the one or more pre-combined images is formed from first and second images where the corresponding illumination schemes include first and second brightfield transmissions using first and second filters of respective first and second colors.

* * * * *